United States Patent

Suzuki et al.

[11] Patent Number: 5,846,962
[45] Date of Patent: Dec. 8, 1998

[54] ANTI-OBESITY AGENTS

[75] Inventors: Kunio Suzuki; Tadashi Nakata; Takeshi Shimizu; Kotaro Enomoto, all of Saitama, Japan

[73] Assignee: The Institute of Physical and Chemical Research, Saitama, Japan

[21] Appl. No.: 897,884

[22] Filed: Jul. 21, 1997

Related U.S. Application Data

[62] Division of Ser. No. 615,299, filed as PCT/JP94/01631, Sep. 30, 1994, Pat. No. 5,710,143.

[30] Foreign Application Priority Data

Sep. 30, 1993 [JP] Japan ................................. 5-245459
Sep. 29, 1994 [JP] Japan ................................. 6-235742

[51] Int. Cl.⁶ ........................ A61K 31/575; C07J 9/00
[52] U.S. Cl. ..................... 514/177; 514/178; 550/542; 550/543; 550/544
[58] Field of Search ................... 514/177, 178; 552/542, 543, 544

[56] References Cited

U.S. PATENT DOCUMENTS

| | | | |
|---|---|---|---|
| 4,202,891 | 5/1980 | Schroepfer, Jr. et al. | 424/242 |
| 4,477,445 | 10/1984 | Philibert et al. | 424/239 |
| 4,897,390 | 1/1990 | Ruhe | 514/177 |
| 5,420,121 | 5/1995 | Suzuki | 514/177 |

FOREIGN PATENT DOCUMENTS

| | | | |
|---|---|---|---|
| 0 133 995 A2 | 8/1984 | European Pat. Off. | ............ C07J 1/00 |
| 0 188 396 A2 | 1/1986 | European Pat. Off. | ............ C07J 1/00 |
| 0 516 530 A1 | 5/1992 | European Pat. Off. | ......... C07J 31/00 |
| 3844408 A1 | 7/1989 | Germany | ............................ C07J 1/00 |
| 5-17065 | 1/1993 | Japan. | |
| 5-170651 (A) | 7/1993 | Japan | ............................ A61K 31/575 |

OTHER PUBLICATIONS

G.B. Forbes et al., Hormonal Response to Overfeeding, *Am. J. Clin. Nutr.;* 49:608–11 (1989).

L. Abrahamsson & H. Hackl, Catabolic Effects and the Influence on Hormonal Variables Under Treatment with Gynodian–Depot® or Dehydroepiandrosterone (DHEA) Oenanthate, *Maturitas,* 3:225–234, (1981).

K. Kusuhara et al., The Pathogenesis of Amenorrhea Related with Simple Weight Loss, *Jpn. J. Fertil. Steril.,* 26:7–15 (1981). (Japanese with English language summary).

*Primary Examiner*—Allen J. Robinson
*Assistant Examiner*—Barbara Badio
*Attorney, Agent, or Firm*—Limbach & Limbach L.L.P.

[57] ABSTRACT

Anti-obesity agents which comprise 3-ketosteroid compounds as an active ingredient are provided. The anti-obesity agents of the present invention have a high anti-obesity effect with little or no side effects and toxicity. Food products which contain anti-obesity agents comprising 3-ketosteroid compounds as an active ingredient, pharmaceutical compositions which comprise 3-ketosteroid compounds as an active ingredient and pharmaceutically acceptable carriers, and methods for preventing and treating obesity which comprise administering an effective amount of a 3-ketosteroid compound to a human are also provided.

7 Claims, 7 Drawing Sheets

INTRAPERITONEAL LIPID IN CDF1 MICE

TIME COURSE OF THE BODY WEIGHTS OF CDF1 MICE

TIME COURSE OF THE BODY WEIGHTS OF CDF1 MICE

INTRAPERITONEAL LIPID IN SD RATS

ANTI-OBESITY AGENTS

This is a divisional of application Ser. No. 08/615,299, filed as PCT/JP94/01631, Sep. 30, 1994, now U.S. Pat. No. 5,710,143.

TECHNICAL FIELD

The present invention relates to anti-obesity agents, more specifically to anti-obesity agents which comprise as an active ingredient 3-ketosteroid compounds having ketone groups at the $C_3$ position of the cholestane skeletons.

BACKGROUND OF THE INVENTION

Obesity is a condition under which the proliferation of tissues of body-composing lipids is increased abnormally. This abnormal condition is produced when energy intake is continuously greater than energy consumption, with the resulting excess energy being converted into neutral lipid which is accumulated in lipid tissues.

Obesity is important as a risk factor of the onset of diseases represented by geriatric diseases from hygienic and cosmetic viewpoints. Harmful influences of obesity have been recognized for a long time in advanced nations. Agents for preventing and/or treating obesity which have been developed until now have side effects or produce unsatisfactory effects.

SP A 5-170651 discloses that anti-obesity agents which comprise 4-cholestene-3-one as an active ingredient have a body lipid-inhibiting effect and present little or no toxicity. However, there still exists a need for more effective anti-obesity agents with less or no side effects and lower toxicity.

Therefore, an object of the present invention is to provide more effective anti-obesity agents with less or no side effects and lower toxicity. Another object of the present invention is to provide food products which are useful for preventing and/or treating obesity.

DISCLOSURE OF THE INVENTION

The inventors found that 3-ketosteroid compounds having ketone groups at the $C_3$ position of the cholestane skeletons produce a high anti-obesity effect and have less or no side effects and lower toxicity. The present invention was accomplished on the basis of these findings. The present invention provides anti-obesity agents which comprise 3-ketosteroid compounds as an active ingredient. The present invention also provides food products which contain anti-obesity agents comprising 3-ketosteroid compounds as an active ingredient.

The present invention further provides pharmaceutical compositions which comprise 3-ketosteroid compounds as an active ingredient and pharmaceutically acceptable carriers.

The present invention also provides a method for preventing and/or treating obesity which comprises administering an effective amount of a 3-ketosteroid compound to a human.

The anti-obesity agents of the present invention show substantially no toxicity and hence are useful.

BEST MODE FOR CARRYING OUT THE INVENTION

Figure 1:
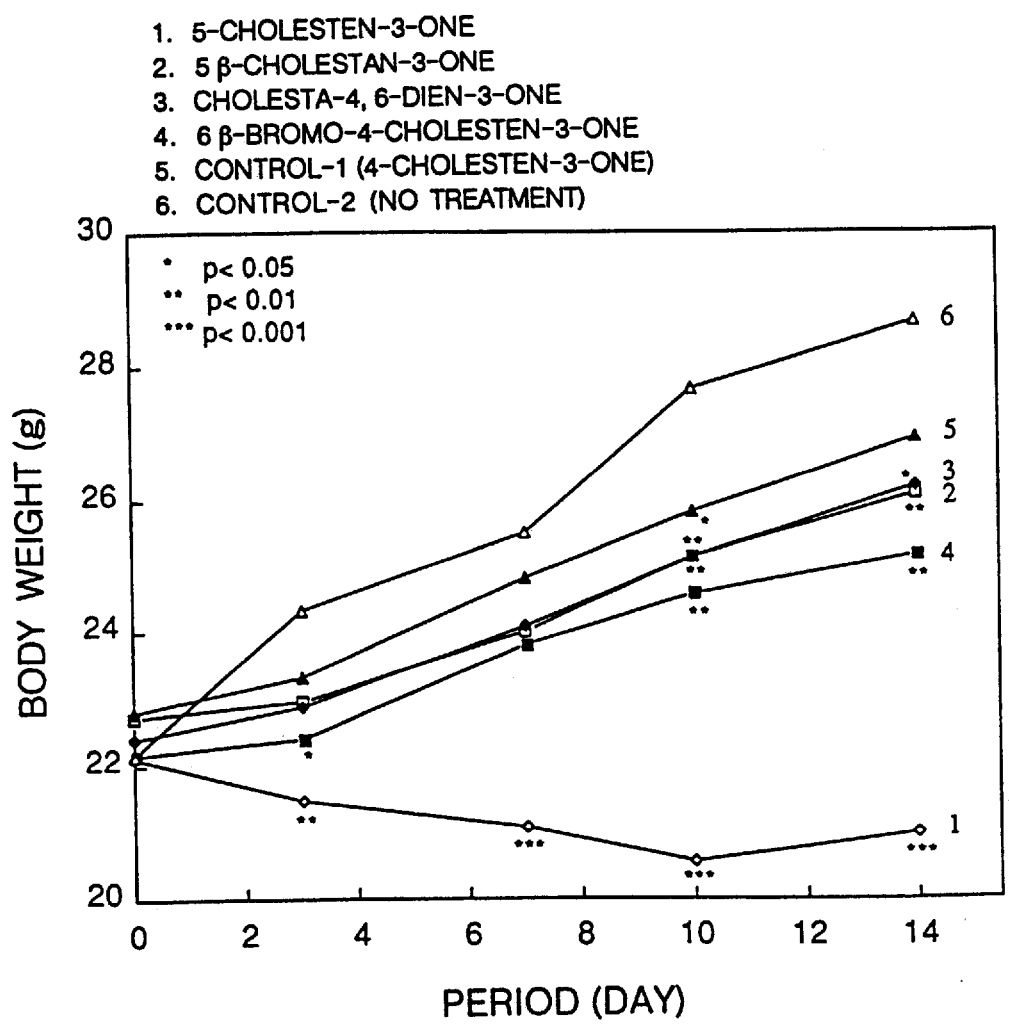
FIG. 1 shows the time course of the average body weights of CDF1 mice in various experimental groups.

The anti-obesity agents of the present invention comprise 3-ketosteroid compounds as an active ingredient. Any 3-ketosteroid compounds can be used, provided that they have an anti-obesity effect. Preferred is at least one compound selected from the group consisting of 5-cholesten-3-one, 5β-cholestan-3-one, cholesta-4,6-dien-3-one, 6β-bromo-4-cholesten-3-one, 6-hydroxy-4-cholesten-3-one and 4-cholestene-3,6-dione. 5-Cholesten-3-one, 6-hydroxy-4-cholesten-3-one and 4-cholestene-3,6-dione are more preferred as having a higher anti-obesity effect.

5-Cholesten-3-one, 5 β-cholestan-3-one, cholesta-4,6-dien-3-one, 6 β-bromo-4-cholesten-3-one, 6-hydroxy-4-cholesten-3-one and 4-cholestene-3,6-dione, which can be used in the present invention, are represented by the following formulae.

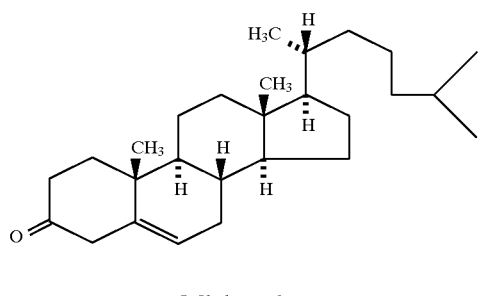

5-Cholesten-3-one

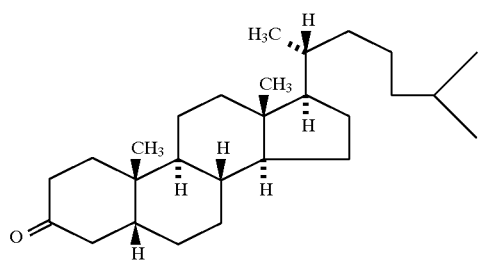

5β-Cholesten-3-one

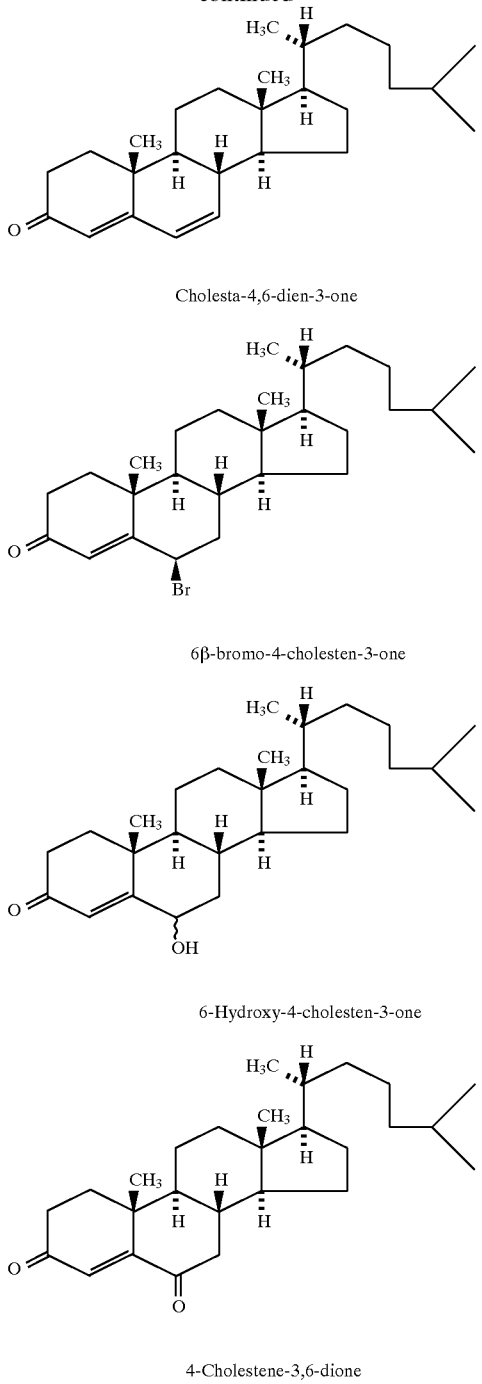

Cholesta-4,6-dien-3-one

6β-bromo-4-cholesten-3-one

6-Hydroxy-4-cholesten-3-one

4-Cholestene-3,6-dione

5-Cholesten-3-one, 5β-cholestan-3-one, cholesta-4,6-dien-3-one, 6 β-bromo-4-cholesten-3-one, 6-hydroxy-4-cholesten-3-one and 4-cholestene-3,6-dione may be synthesized chemically, produced biologically by culturing a microorganism capable of producing a desired compound, or synthesized with an enzyme derived from a microorganism. Alternatively, commercially available ones produced by any one of these methods may be used. For example, 5-cholesten-3-one can be produced using cholesterol as a starting material by the method of Cheng et al. (Y.-s. Cheng, W. L. Liu and S.-h. Chen, Synthesis; 1980, 223) or using 4-cholesten-3-one as a starting material by the method of Ringold et al. (H. J. Ringold and S. K. Malhotra, Tetrahedron Lett., 1962, 669). 5β-Cholestan-3-one can be produced using 4-cholesten-3-one as a starting material by the method of Tsuji et al. (N. Tsuji, J. Suzaki, and M. Shiota, J. Org. Chem., 45: 2729, 1980). Cholesta-4,6-dien-3-one can be produced using 4-cholesten-3-one as a starting material by a combination of the method of Chowdhury et al. (P. K. Chowdhury, R. P. Sharma, and J. N. Barua, Tetrahedron Lett., 24: 3383, 1983) and that of Minami et al. (I. Minami, K. Takahashi, I. Shimizu, and J. Tsuji, Tetrahedron, 42: 2971, 1986). 6β-Bromo-4-cholesten-3-one can be produced by reacting the dienol acetate prepared by the method of Chowdhury et al. (ibid.) with bromine in a dioxane-phosphate buffer (pH 7.0). 6-Hydroxy-4-cholesten-3-one can be produced by reacting pyridinium chlorochromate with 5,6-epoxycholesterol. 4-3'-Cholestene-3,6-dione can be produced using 4-cholesten-3-one as a starting material by a combination of the method of Hevl and Herr (F. W. Hevl and M. E. Herr, J. Am. Chem. Soc., 75: 1918, 1953) and that of Malhotra et al. (S. K. Malhotra, J. J. Hostynek and A. F. Lundin, J. Am. Chem. Soc., 90: 6565, 1968).

While not being limited to a specific theory, it is assumed that the 3-ketosteroid compounds produce the anti-obesity effect by any one or more of the following mechanisms.

(1) Inhibition of the formation of bile acid micelles in the intestines and competition against the dissolving of lipids in bile acid micelles.

(2) Inhibition of the formation of lipoprotein membranes in intestinal tissues and competition against the incorporation of lipids into lipoproteins.

(3) Inhibition of the synthesis of cholesterols in the livers and competition against the effects of cholesterols.

The anti-obesity agents of the present invention can be added to food products. In this case, the 3-ketosteroid compounds may be added directly to food products. Alternatively, the 3-ketosteroid compounds may be added to fats and/or oils and the resulting mixture may be used to produce food products. Examples of the food products include any foods and drinks including natural and processed products, feeds for domestic animals and cultured fish and the like. The 3-ketosteroid compounds can be added in amounts of 1–5,000 mg to 100 g of a food product or fat and/or oil. The anti-obesity agents of the present invention may be formulated in the form of solutions, suspensions, powders, granules, capsules or the like and the formulated preparations may be added to food products or fats and/or oils.

The anti-obesity agents of the present invention can be formulated in pharmaceutical compositions for use. In this case, the route of administration of the pharmaceutical compositions includes but is not limited to oral, intravenous, intraperitoneal, subcutaneous and intramuscular administrations. Oral administration is preferred. In the case of oral administration, the 3-ketosteroid compounds may be administered with or without pharmaceutically acceptable carriers in the form of solutions, suspensions, powders, granules, tablets, capsules or the like. Examples of the carriers include any conventionally used ones, for example, sugars such as lactose, sucrose and glucose, starch, inorganic compounds such as calcium carbonate and calcium sulfate, crystalline cellulose, distilled water, purified water, sesame oil, soybean oil, corn oil, olive oil, cotton seed oil and the like. In formulating the pharmaceutical compositions, additives such as binders, lubricants, dispersers, suspending agents, emulsifying agents, diluents, buffering agents, antioxidants, bacteriostats and the like may be used. In the case where the pharmaceutical compositions are used as injections, an appropriate buffering agent, tonicity agent and the like may be added and the resulting mixtures may be dissolved in oils such as vegetable oils. The pharmaceutical compositions may be used in admixture or combination with other medicaments. The pharmaceutical compositions may be sterilized.

The dose of the anti-obesity agents of the present invention can be varied depending on the age and sex of the patient, severity of the disease to be treated, the route of administration, the number of administrations, the dosage form and the like. In the case of oral administration, the dose of the 3-ketosteroid compounds is appropriately in the range from 1 to 1,000 mg/kg body weight/day for adult patients.

The present invention will be explained in greater detail with reference to the following examples, which are intended to be illustrative of but not limiting the scope of the present invention.

[Preparation Example 1]

5β-Cholestan-3-one was prepared using 4-cholesten-3-one (Aldrich Co.) as a starting material by the method of Tsuji et al. (N. Tsuji, J. Suzaki, and M. Shiota, J. Org. Chem., 45: 2729, 1980) (yield: 99%).

[Preparation Example 2]

Dienol acetate was synthesized by the method of Chowdhury et al. (P. K. Chowdhury, R. P. Sharma, and J. N. Barua, Tetrahedron. Lett., 24: 3383; 1983) as follows:

Trimethylsilyl chloride (5.5 ml) was added to a solution of 4-cholesten-3-one (3.84 g, 10 mmol, Aldrich Co.) in an acetic anhydride solution (40 ml). The mixture was refluxed under heating in argon gas for 3 hours. After vacuum concentration, the residue was dissolved in ethyl acetate, washed with a saturated aqueous solution of sodium carbonate and a saturated saline solution and dried over magnesium sulfate. The solvents were distilled off and the residue was subjected to silica gel column chromatography to yield dienol acetate (3.3 g, yield: 88%).

Then, cholesta-4,6-dien-3-one was prepared from the dienol acetate by the method of Minami et al. (I. Minami, K. Takahashi, I. Shimizu, and J. Tsuji, Tetrahedron, 42: 2971, 1986) (yield: 83%).

[Preparation Example 3]

The dienol acetate prepared in Preparation Example 2 (3.77 g, 8.8 mmol) was dissolved in 140 ml of dichloromethane and a dioxane(70 ml)-phosphate buffer (pH 7.0, 70 ml) was added. The mixture was then cooled at 0° C. and $Br_2$ (841 g μl, 8.8 mmol) was added dropwise under stirring. The resulting solution was stirred at 0° C. for 100 minutes and a mixture of an aqueous solution of sodium thiosulfate (1.5 g) and an aqueous solution of sodium bicarbonate (3.0 g) was then added. The resulting mixture was stirred for additional 15 minutes. The organic layer was separated, washed with a saturated aqueous solution of sodium carbonate and a saturated saline solution and dried over magnesium sulfate. After the solvents were distilled off under vacuum, the residue was subjected to silica gel column chromatography to yield 6β-bromo-4-cholesten-3-one (3.23 g, yield: 80%).

[Preparation Example 4]

Dichloromethane (50 ml) was added to pyridinium chlorochromate (2.78 g, 12.9 mmol) and molecular shieves (3A) (4.37 g) and the mixture was stirred under a nitrogen atmosphere at room temperature for 15 minutes. To the resulting mixture was added a dichloromethane solution (30 ml) of 5,6-epoxycholesterol (α:β=5:1) (3.323 g, 8.6 mmol) prepared by the method of Fieser and Fieser (L. F. Fieser and H. Fieser, Reagents for Organic Synthesis, Vol. 1: 136, 1967) and the mixture was stirred for 3 hours. Ether (300 ml) was added to the reaction solution and the resulting solution was filtered through silica gel-magnesium sulfate. The organic layer was washed twice with 50 ml of a saturated saline solution and dried. The solvents were distilled off and the residue was purified by column chromatography. 6-Hydroxy-4-cholesten-3-one (α:β=5:1) was obtained as a colorless crystal from the hexane-ethyl acetate (5:1) eluate (yield: 51.7%).

[Preparation Example 5]

4-Cholesten-3,6-dione was prepared using 4-cholesten-3-one (Aldrich Co.) as a starting material by reference to the method of Hevl and Herr (F. W. Hevl and M. E. Herr, J. Am. Chem. Soc., 75: 1918, 1953) and that of Malhotra et al. (S. K. Malhotra, J. J. Hostynek and A. F. Lundin, J. Am. Chem. Soc., 90: 6565, 1968). Stated specifically, pyrrolidine (2.85 g) was added to a benzene solution (50 ml) of 4-cholesten-3-one (3.84 g) and the mixture was refluxed under heating for 24 hours. After cooling, the solvent and the excess pyrrolidine were distilled off under vacuum. Upon recrystallization from methanol, a colorless crystal of dienamine (4.16 g) was obtained. Cupric acetate (100 mg) was added to a benzene-methanol (500:10) solution of the dienamine (4.16 g) and air was introduced into the mixture for 24 hours. Then, a 2% aqueous solution (20 ml) of acetic acid was added and the mixture was stirred for 30 minutes and washed successively with water, a 1% sodium carbonate solution and a saturated saline solution. The resulting residue was dried, filtered and subjected to silica gel column chromatography (hexane:ethyl acetate=10:1) to yield a colorless crystal of 4-cholestene-3,6-dione (3.23 g).

[Example 1]

A. Test Method

5-Cholesten-3-one purchased from Sigma Co., 5β-cholestan-3-one as prepared in Preparation Example 1, cholesta-4,6-dien-3-one as prepared in Preparation Example 2 and 6β-bromo-4-cholesten-3-one as prepared in Preparation Example 3 were used as test compounds; and 4-cholesten-3-one purchased from Aldrich Co. was used as a comparative compound. The following examination was carried out with these compounds.

1. Animals and Feeding Conditions

Six male CDF1 mice (5 weeks, BALB/c×DBA/2) purchased from Japanese Charles River Co., Ltd. were used in each experimental group.

All the mice were divided into experimental groups and placed in aluminum cages (22 cm×33 cm×11 cm height). They were fed and allowed to feed and water ad libitum at a temperature of 24°±1° C. and a relative humidity of 55±5% for 2 weeks in a laboratory where light and darkness were controlled change every 12 hours. Each cage and floor mat (white flakes) were exchanged twice a week.

2. Preparation of Test Feeds

A synthetic feed (powder feed), or modified AIN (Oriental Yeast Co.), was used as a basic feed to prepare test feeds as described below in 1)–6). The basic feed was composed of 22.8% proteins, 54.1% carbohydrates, 6.0% lipids, 4.9% fibers, 2.9% ash and 8.7% water (calorie: 1,523 KJ).

The addition of a test compound at 0.5 wt % to the basic feed corresponds to the administration of the test compound at 995 mg/kg body weight/day per mouse on average. The test feeds were stored at 4° C. after preparation and a fresh one was daily provided.

1) Feed for 5-cholesten-3-one group: 5-Cholesten-3-one purchased from Sigma Co. was added to the basic feed at 0.5 wt %.

2) Feed for 5β-cholestan-3-one group: 5β-Cholestane-3-one was added to the basic feed at 0.5 wt %.

3) Feed for cholesta-4,6-dien-3-one group: Cholesta-4,6-dien-3-one was added to the basic feed at 0.5 wt %.

4) Feed for 6β-bromo-4-cholesten-3-one group: 6β-Bromo-cholesten-3-one was added to the basic feed at 0.5 wt %.

5) Feed for control-1 group: 4-Cholesten-3-one was added to the basic feed at 0.5 wt %.

6) Feed for control-2 group: Nothing was added to the basic feed.

3. Test Items

The mice were weighed at given intervals of time and the average values of the various experimental groups were determined. In addition, the feed consumptions were measured at given intervals of time and the average feed efficiencies (increase in body weight per 100 g of feed) of the various experimental groups were determined. After the end of the feeding, all the mice were anesthetized to death with carbon dioxide gas and autopsied. The brains, lungs, hearts, livers, spleens, kidneys, testis, adrenals and intraperitoneal lipids were weighed and the average values of the various experimental groups were determined.

B. Test Results (1) Measurement of the change in body weight and the feed consumption The changes in the average body weights of the various experimental groups are shown in FIG. 1. In FIG. 1, *,  and * show the presence of a significant difference from the non-treated control-2 group at probability (p) levels of <5%, <1% and <0.1%, respectively, in a t-test.

The increase in body weight was greatly inhibited in the 5-cholesten-3-one group, 5β-cholestan-3-one group, cholesta-4,6-dien-3-one group and 6β-bromo-4-cholesten-3-one group, compared to the non-treated control-2 group. The inhibition of the increase in body weight in these groups was also greater than in the control-1 group treated with 4-cholesten-3-one. In particular, the 5-cholesten-3-one group showed a remarkable inhibition of the increase in body weight. The average body weight of the 5-cholesten-3-one group decreased up to the 10th day of feeding, increased a little at day 14 and leveled off thereafter.

In conclusion, the test compounds, 5-cholesten-3-one, 5β-cholestan-3-one, cholesta-4,6-dien-3-one and 6β-bromo-4-cholesten-3-one are more effective in inhibiting the increase in body weight than the comparative compound 4-cholesten-3-one.

The average feed efficiencies of the various experimental groups are shown in Table 1. Table 1 shows clearly that the groups with the lower increase in body weight had lower feed efficiencies. Therefore, it was found that the inhibitory effect of the test compounds on the increase in body weight was not due to the diminution of appetite.

TABLE 1

Feed Efficiencies of CDF1 Mice

| Experimental Group | 1 week | 2 week |
|---|---|---|
| 1. 5-Cholesten-3-one group | −3.32 | −0.39 |
| 2. 5β-Cholestan-3-one group | 3.53 | 6.11 |
| 3. Cholesta-4,6-dien-3-one group | 5.13 | 5.77 |
| 4. 6β-bromo-4-cholesten-3-one group | 5.49 | 4.48 |
| 5. Control-1 (4-cholesten-3-one) group | 5.85 | 5.99 |
| 6. Control-2 (non-treated) group | 7.87 | 6.98 |

(2) Measurement of intraperitoneal lipid

Figure 2:
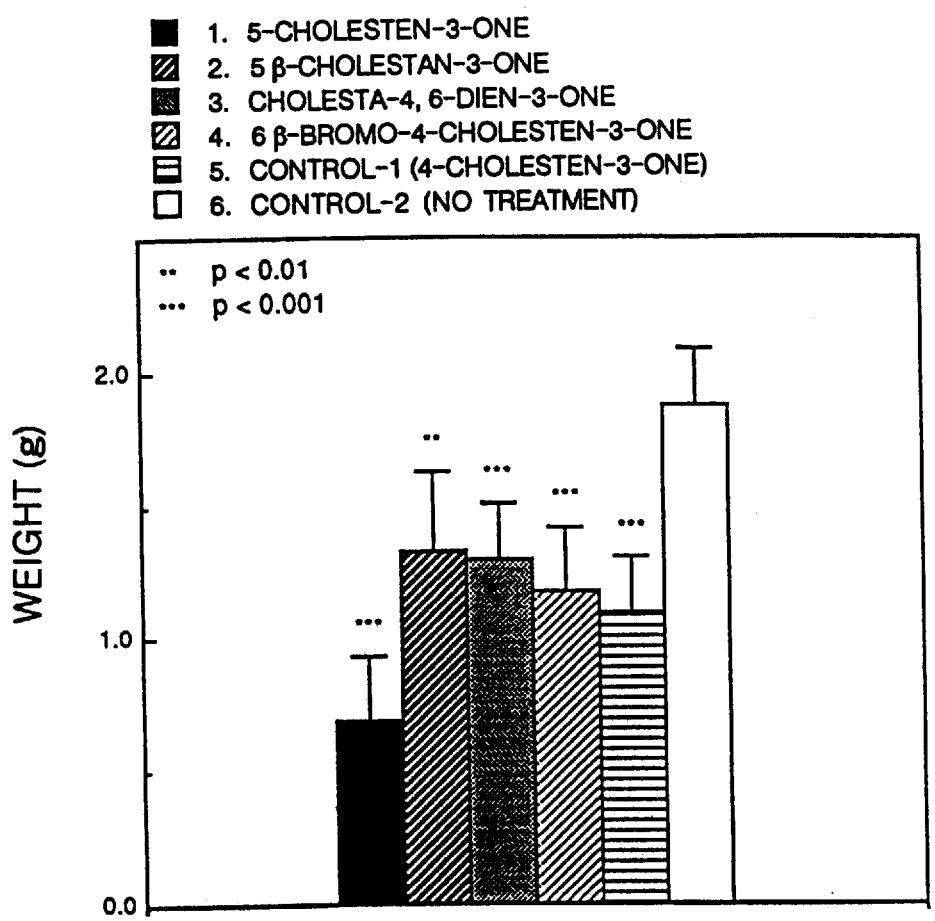
FIG. 2 shows the average intraperitoneal lipids in CDF1 mice in various experimental groups at the end of feeding.

The average intraperitoneal lipids in the various experimental groups are shown in FIG. 2. The intraperitoneal lipid in all the mice treated with the test compounds was smaller with a statistically significant difference than in the non-treated control-2 group. In FIG. 2,  and * show the presence of a significant difference from the non-treated control-2 group at probability (p) levels of <1% and <0.1%, respectively, in a t-test. The differences in intraperitoneal lipid between the test compound-treated groups and the non-treated control-2 group were in substantial proportion to the levels of the inhibition of the increase in body weight. Therefore, it was found that the administration of the test compounds results in the accumulation of smaller amounts of body lipids, which is one of the primary reasons for the inhibition of the increase in body weight.

(3) Measurement of organ weights

The average organ weights are shown in Table 2. The values in Table 2 are represented by relative weights per 100 g of body weight. The symbols *, ** and * show the presence of a significant difference the non-treated control-2 group at probability (p) levels of <5%, <1% and <0.1%, respectively, in a t-test. When the body weight decreases, a decrease in the amount of body lipid is followed by decrease in the amount of muscles. On the other hand, the amounts of main organs which fulfill important functions in the body will not decrease as much, so the relative weights of the main organs will increase.

A relative increase in the weight of spleen was observed in the 5-cholesten-3-one group, 5β-cholestan-3-one group and 6β-bromo-4-esten-3-one group. In the 5-cholesten-3-one group, a relative increase in the weights of brain and testis was observed. In the 5β-cholestan-3-one group, a relative decrease in the weight of lung was also observed. In the control-1 group treated with 4-cholesten-3-one, a relative increase in the weights of spleen and testis was observed. normal values were not recognized in any groups, suggesting that the test compounds have little or no toxicity and side effects.

TABLE 2

Relative Weights of Main Organs in CDF1 Mice[a]

| Experimental Group | Brain (g) | Heart (g) | Lung (g) | Liver (g) | Spleen (g) | Kidney (g) | Adrenal (mg) | Testis (g) |
|---|---|---|---|---|---|---|---|---|
| 1 | 1.86*** | 0.53 | 0.98 | 4.88 | 0.33** | 1.39 | 17.17 | 0.76* |
| 2 | 1.54 | 0.54 | 0.83* | 4.24 | 0.37*** | 1.61 | 14.88 | 0.64 |
| 3 | 1.53 | 0.59 | 0.91 | 4.14 | 0.29 | 1.58 | 14.42 | 0.66 |
| 4 | 1.57 | 0.55 | 1.00 | 5.00 | 0.30* | 1.54 | 14.70 | 0.66 |
| 5 | 1.48 | 0.51 | 0.87 | 4.01 | 0.37*** | 1.56 | 15.67 | 0.69* |
| 6 | 1.47 | 0.54 | 0.98 | 4.50 | 0.26 | 1.63 | 16.62 | 0.59 |

[a]the numerical values are the average for six mice in each group.

None of the experimental groups had aberrations such as abnormalities in the colors of the main organs and the occurrence of tumor. All the mice seemed to be normal to the naked eye.

In regard to general appearance, the 5-cholesten-3-one group mice had a sign of emaciation but mice in the other groups showed no abnormalities in the color of hair and behavior. They also did not develop any abnormal symptoms such as diarrhea.

In conclusion, the results of measurement of the main organ weights and the autopsical finding with the naked eye demonstrated that the test compounds have little of no side effects or toxicity.

[Example 2]

A. Test Method

A test feed was prepared by adding 0.5 wt % of a test compound (6-hydroxy-4-cholesten-3-one as prepared in Preparation Example 1) to a basic feed, or modified AIN (Oriental Yeast Co.). Feeds for control-1 and -2 groups were prepared by the same method as in Example 1. The other procedures were the same as in Example 1.

B. Test Results (1) Change in body weight

Figure 3:
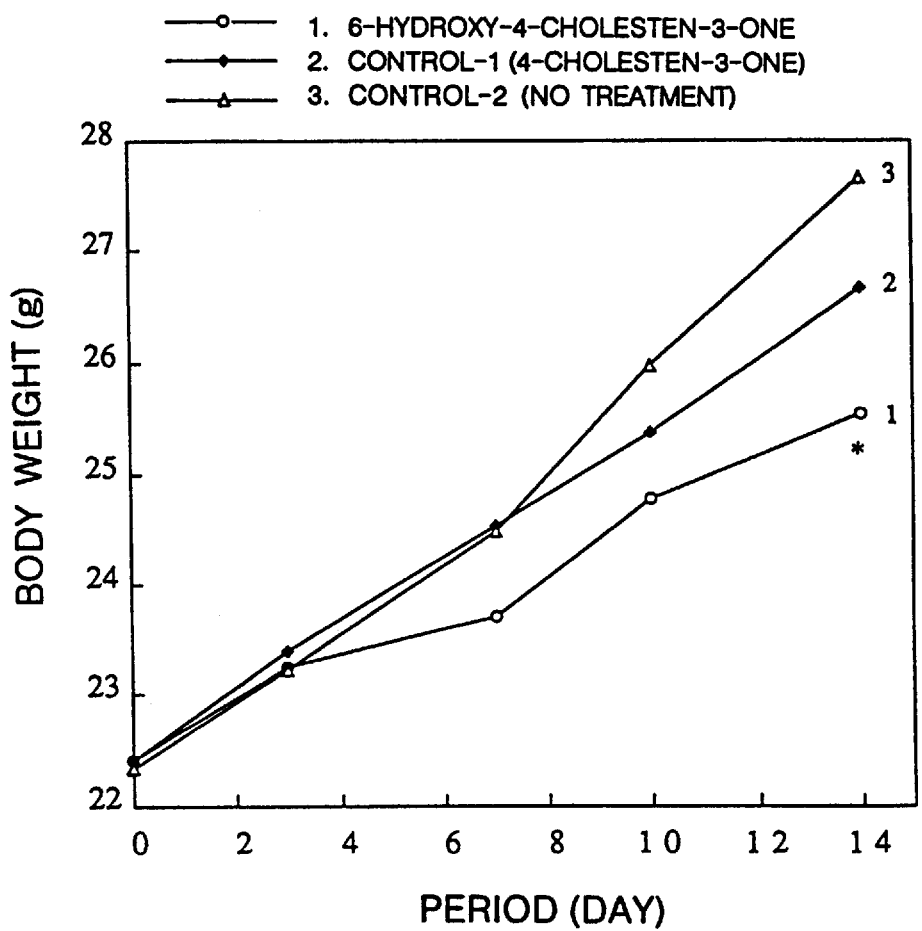
FIG. 3 shows the time course of the average body weight of CDF1 mice treated with 6-hydroxy-4-cholestene-3-one.

The changes in the average body weights of the various experimental groups are shown in FIG. 3. In FIG. 3, * shows the presence of a significant difference from the non-treated control-2 group at a probability (p) level of <5% in a t-test. The increase in body weight was significantly inhibited in the 6-hydroxy-4-cholesten-3-one group. After 14 days of the treatment, the increase in body weight of the 6-hydroxy-4-cholesten-3-one group was significantly different from that of the non-treated control-2 group and smaller than that of the positive control 4-cholesten-3-one group (control-1 group).

In conclusion, the test compound 6-hydroxy-4-cholesten-3-one is more effective in inhibiting the increase in body weight than the comparative compound, 4-cholesten-3-one.

(2) Change in feed consumption

The feed efficiencies of the various experimental groups are shown in Table 3. The feed efficiencies of the various experimental groups were substantially consistent with the tendency of increasing body weight. Therefore, it was confirmed that the inhibitory effect of the 6-hydroxy-4-cholesten-3-one on the increase in body weight was due to the reduction in feed efficiency rather than to the decrease in feed intake.

TABLE 3

Feed Efficiencies of CDF1 Mice

| Experimental Group | 1 week | 2 week |
|---|---|---|
| 1. 6-hydroxy-4-cholesten-3-one group | 1.76 | 3.29 |
| 2. Control-1 (4-cholesten-3-one) group | 4.68 | 5.84 |
| 3. Control-2 (non-treated) group | 5.52 | 7.64 |

(3) Measurement of intraperitoneal lipid

Figure 4:
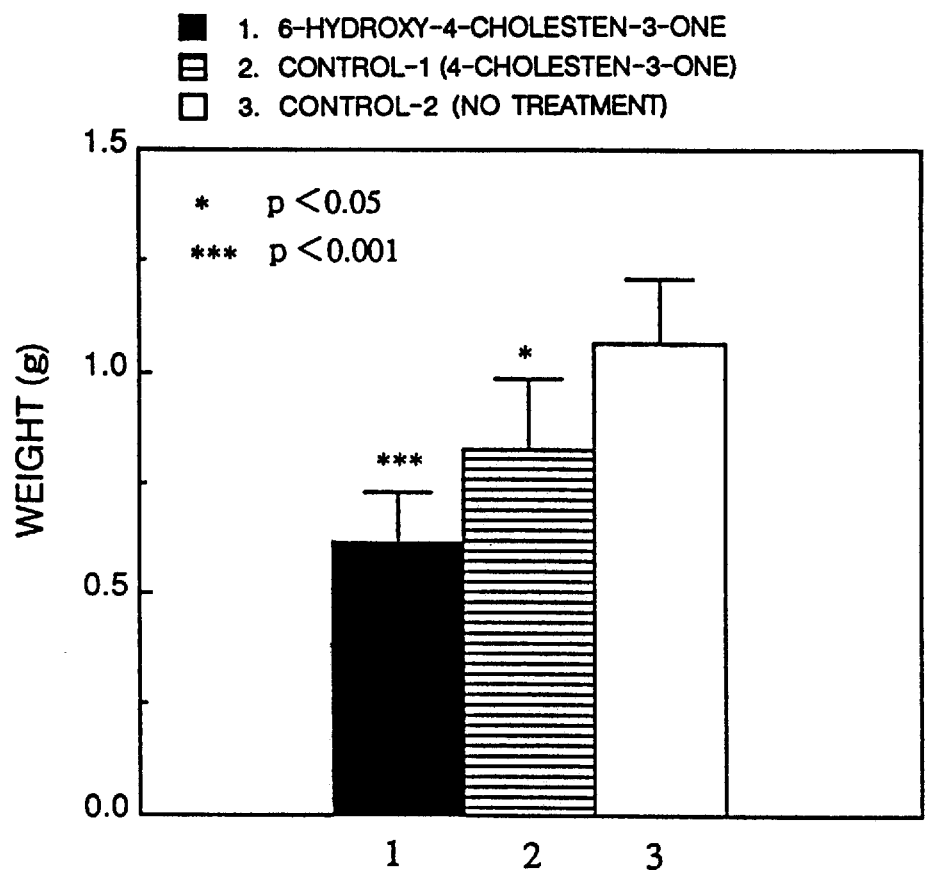
FIG. 4 shows the average intraperitoneal lipid in 6-hydroxy-4-cholestene-3-one-treated CDF1 mice at the end of feeding.

The average intraperitoneal lipids in the various experimental groups are shown in FIG. 4. In FIG. 4, * and *** show the presence of a significant difference from the non-treated control-2 group at probability (p) levels of <5% and <0.1%, respectively, in a t-test. The intraperitoneal lipid in the 6-hydroxy-4-cholesten-3-one group was significantly smaller than in the non-treated control-2 group. Therefore, it was found that 6-hydroxy-4-cholesten-3-one is effective in inhibiting the accumulation of body lipids, particularly intraperitoneal lipids.

(4) General conditions and autopsical finding

The general conditions of the 6-hydroxy-4-cholesten-3-one group were as normal as in the non-treated control-2 group in terms of the color of hair, feces, behavior and appetite. In anatomical examination after the treatment, no pathological abnormalities in organs were observed with the naked eye. The organ weights (relative weights per 100 g of body weight) of the various experimental groups are shown in Table 4. In Table 4, *,  and * show the presence of a significant difference from the non-treated control-2 group at probability (p) levels of <5%, <1% and <0.1%, respectively, in a t-test.

The weights of the brain, liver and spleen in the 6-hydroxy-4-cholesten-3-one group were a little greater than in the non-treated control-2 group. However, in the absence of any pathological changes in these organs, it was verified that there was no toxic influence.

In conclusion, it was shown that 6-hydroxy-4-cholesten-3-one has little or no toxicity.

TABLE 4

Relative Weights of Main Organs in CDF1 Mice[a]

| Experimental Group | Brain (g) | Heart (g) | Lung (g) | Liver (g) | Spleen (g) | Kidney (g) | Adrenal (mg) | Testis (g) |
|---|---|---|---|---|---|---|---|---|
| 1 | 1.72** | 0.55 | 0.74 | 5.00** | 0.33** | 1.49 | 11.53 | 0.70 |
| 2 | 1.63 | 0.55 | 0.78 | 4.90 | 0.38*** | 1.65 | 11.83 | 0.71 |
| 3 | 1.58 | 0.53 | 0.65 | 4.73 | 0.27 | 1.66 | 15.39 | 0.60 |

[a]the numerical values are the average for six mice in each group.

The results demonstrated that 6-hydroxy-4-cholesten-3-one exhibits an anti-obesity effect by inhibiting the accumulation of body lipids and that it has little or no toxicity.

[Example 3]

A. Test Method

A test feed was prepared by adding 0.5 wt % of a test compound (4-estene-3,6-dione as prepared in Preparation Example 5) to a basic feed, or modified AIN (Oriental Yeast Co.). Feeds for control-1 and -2 groups were prepared by the same method as in Example 1. The other procedures were the same as in Example 1.

B. Test Results (1) Change in body weight

Figure 5:
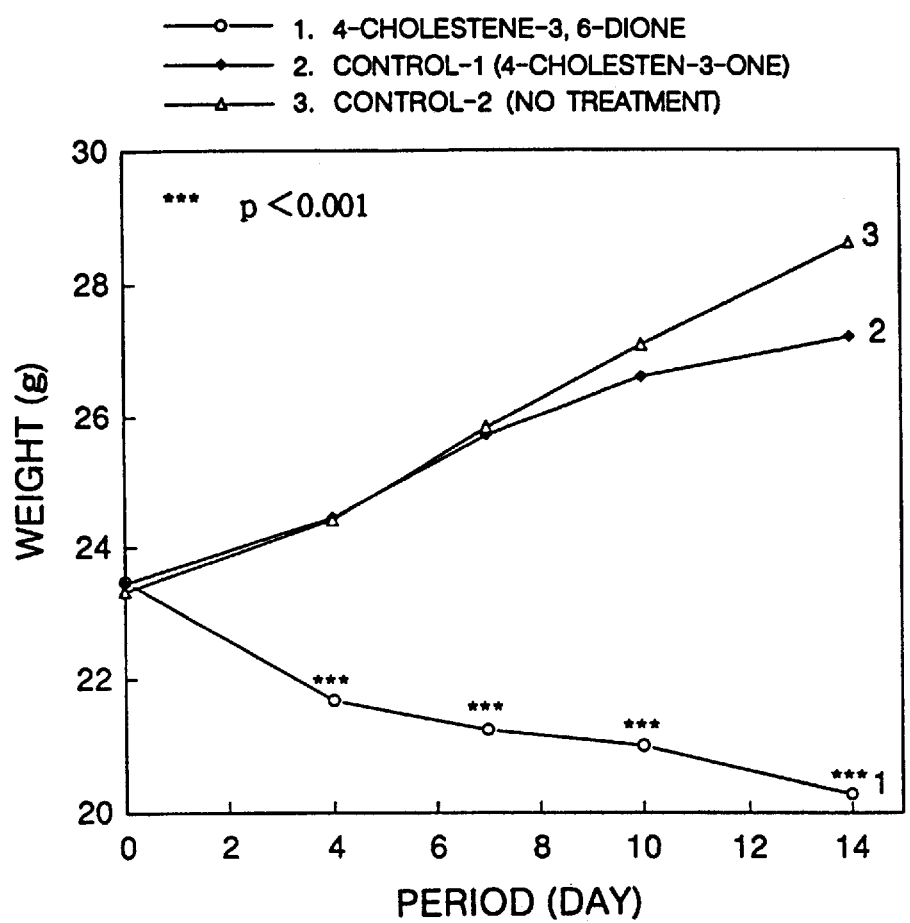
FIG. 5 shows the time course of the average body weight of CDF1 mice treated with 4-cholestene-3,6-dione.

The changes in the average body weights of the various experimental groups are shown in FIG. 5. In FIG. 5, *** shows the presence of a significant difference from the non-treated control-2 group at a probability (p) level of <0.1% in a t-test. The increase in body weight was significantly inhibited in the 4-cholestene-3,6-dione group. After 4 days of the treatment, the body weight of the 4-cholestene-3,6-dione group was significantly different from that of the non-treated control-2 group and smaller than that of the positive control 4-cholesten-3-one group (control-1 group).

logical changes in these organs, it was verified that there was no toxic influence.

In conclusion, it was shown that 4-cholestene-3,6-dione has little or no toxicity.

TABLE 6

Relative Weights of Main Organs in CDF1 Mice[a]

| Experimental Group | Brain (g) | Heart (g) | Lung (g) | Liver (g) | Spleen (g) | Kidney (g) | Adrenal (mg) | Testis (g) |
|---|---|---|---|---|---|---|---|---|
| 1 | 2.05** | 0.60 | 0.70 | 4.67 | 0.32 | 1.31** | 13.35 | 0.87** |
| 2 | 1.58 | 0.52 | 0.82 | 4.60** | 0.31 | 1.59 | 16.37** | 0.63 |
| 3 | 1.50 | 0.56 | 0.76 | 4.86 | 0.29 | 1.64 | 10.60 | 0.65 |

[a]the numerical values are the average for six mice in each group.

In conclusion, the test compound 4-cholestene-3,6-dione is more effective in inhibiting the increase in body weight than the comparative compound 4-cholesten-3-one.

(2) Change in feed consumption

The feed efficiencies of the various experimental groups are shown in Table 5. The feed efficiencies of the various experimental groups were substantially consistent with the tendency of increasing body weight. Therefore, it was confirmed that the inhibitory effect of 4-cholestene-3,6-dione on the increase in body weight was due to the reduction in feed efficiency rather than to the decrease in feed intake.

TABLE 5

Feed Efficiencies of CDF1 Mice

| Experimental Group | 1 week | 2 week |
|---|---|---|
| 1. 4-Choelstene-3,6-dione group | −7.24 | −3.28 |
| 2. Control-1 (4-cholesten-3-one) group | 6.40 | 4.04 |
| 3. Control-2 (non-treated) group | 8.77 | 10.17 |

(3) Measurement of intraperitoneal lipid

Figure 6:
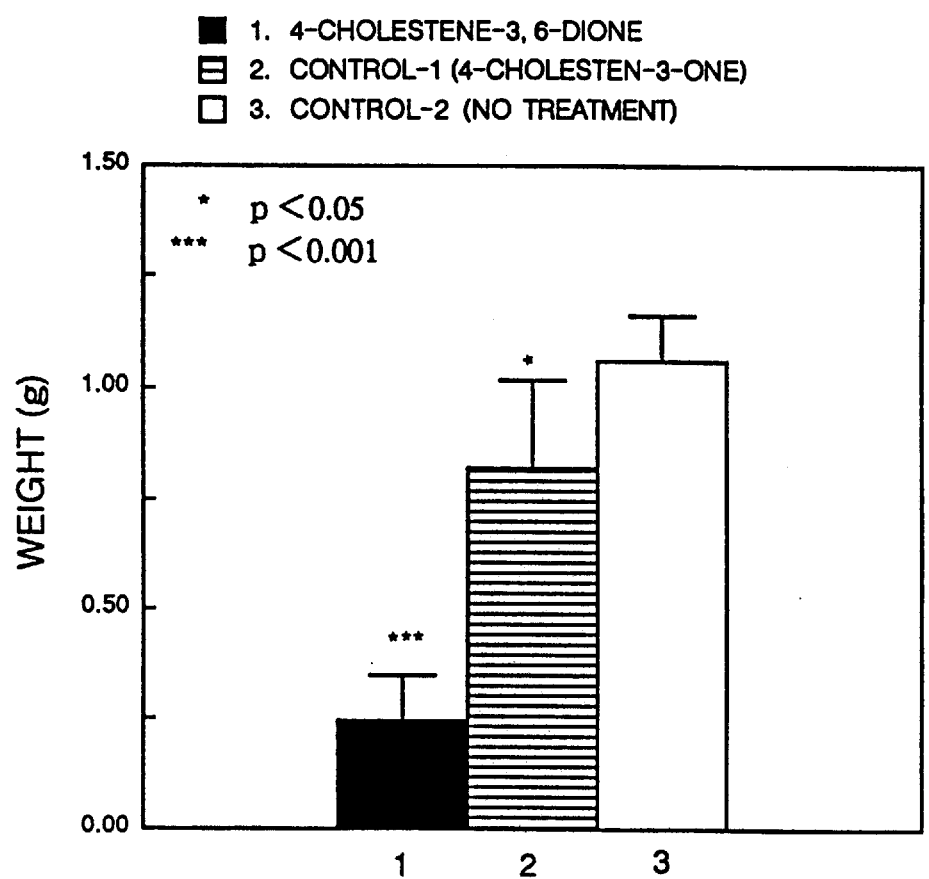
FIG. 6 shows the average intraperitoneal lipid in CDF1 mice treated with 4-cholestene-3,6-dione.

The average intraperitoneal lipids in the various experimental groups are shown in FIG. 6. In FIG. 6, * and *** show the presence of a significant difference from the non-treated control-2 group at probability (p) levels of <5% and <0.1%, respectively, in a t-test. The intraperitoneal lipid in the 4-cholestene-3,6-dione group was significantly smaller than that in the non-treated control-2 group and the effect of 4-cholestene-3,6-dione was stronger than that of 4-cholesten-3-one. Therefore, it was found that 4-cholestene-3,6-dione is more effective in inhibiting the accumulation of body lipids, particularly intraperitoneal lipids.

(4) General conditions and autopsical finding

The general conditions of the 4-cholestene-3,6-dione group were as normal as in the non-treated control-2 group in terms of the color of hair, feces, behavior and appetite. In anatomical examination after the treatment, no pathological abnormalities in organs were observed with the naked eye. The organ weights (relative weights per 100 g of body weight) of the various experimental groups are shown in Table 6. In Table 6,  and * show the presence of a significant difference from the non-treated control-2 group at probability (p) levels of <1% and <0.1%, respectively, in a t-test.

The weights of the brain, kidney and testis in the 4-cholestene-3,6-dione group had significant differences from the non-treated control-2 group but the differences were very small. In addition, in the absence of any patho-

[Example 4]

A. Test Method

5-Cholesten-3-one purchased from Sigma Co. was used as a test compound and 4-cholesten-3-one purchased from Aldrich Co. was used as a comparative compound. The following examination was carried out with these compounds.

1. Animals and Feeding Conditions

Three male Sprague-Dawley (SD) rats (4 weeks) purchased from Japanese Charles River Co., Ltd. were used in each experimental group.

2. Preparation of Test Feeds

A test feed was prepared by adding 0.5 wt % of a test compound (5-cholesten-3-one) to a basic feed, or modified AIN (Oriental Yeast Co.). A feed for control-1 group was prepared by the same method as above except that the comparative compound 4-cholesten-3-one was used instead of 5-cholesten-3-one.

3. The other procedures were the same as in Example 1.

B. Test Results (1) Change in body weight and intraperitoneal lipid

Figure 7:
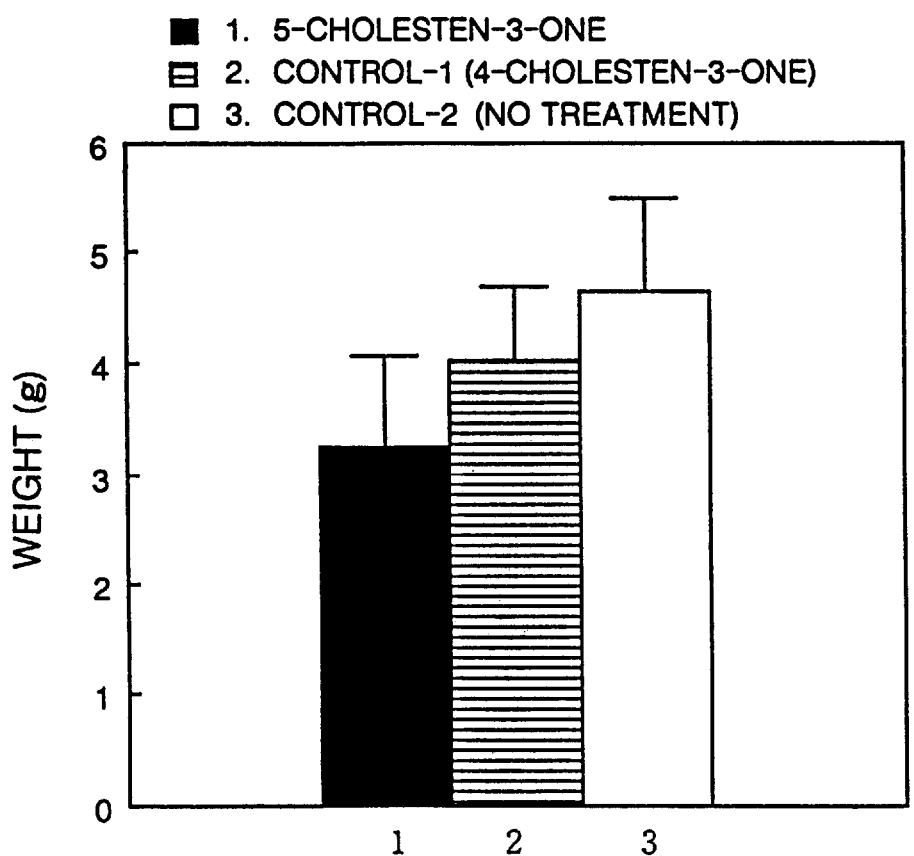
FIG. 7 shows the average intraperitoneal lipid in SD rats treated with 5-cholestene-3-one.

At day 14 after the treatment, there was no significant difference in body weight between the experimental groups. However, the intraperitoneal lipid in the 5-cholesten-3-one group was smaller than that in the 4-cholesten-3-one group (control-1 group) as shown in FIG. 7.

(2) General conditions and autopsical finding

The general conditions of the 5-cholesten-3-one group were as normal as in the 4-cholesten-3-one group (control-1 group) in terms of the color of hair, feces, behavior and appetite.

The organ weights (relative weights per 100 g of body weight) of the experimental groups are shown in Table 7. In Table 7, * and ** show the presence of a significant difference from the non-treated control-2 group at probability (p) levels of <5% and <1%, respectively, in a t-test. In the group of the comparative compound 4-cholesten-3-one, a significant enlargement of the adrenal, as well as congestion and swelling of the spleen were observed. In contrast, the 5-cholesten-3-one group did not show any more abnormalities in the main organs than the non-treated control-2 group. Although there were significant differences in the lung weight of the 4-cholesten-3-one group and the brain weights of the 4-cholesten-3-one group and the 5-cholesten-3-one group in a t-test, the differences were small and within the normal range, therefore, they were not considered to have been caused by any toxic effects.

TABLE 7

Relative Weights of Main Organs in SD Rats[b]

| Experimental Group | Brain (g) | Heart (g) | Lung (g) | Liver (g) | Spleen (g) | Kidney (g) | Adrenal (mg) | Testis (g) |
|---|---|---|---|---|---|---|---|---|
| 1 | 0.77** | 0.37 | 0.65 | 5.10 | 0.27 | 0.94 | 13.63 | 0.85 |
| 2 | 0.74* | 0.39 | 0.64* | 5.05 | 0.33* | 0.95 | 26.90** | 0.95 |
| 3 | 0.81 | 0.41 | 0.60 | 5.02 | 0.26 | 0.99 | 13.39 | 0.92 |

[b]the numerical values are the average for three rats in each group.
Experimental Group 1: 5-Cholesten-3-one group
Experimental Group 2: Control-1 (4-cholesten-3-one) group
Experimental Group 3: Control-2 (non-treated) group As described above, the comparative compound 4-cholesten-3-one exhibits side effects on SD rats, such as an enlargement of the adrenal, as well as congestion and swelling of the spleen; on the other hand, 5-cholesten-3-one does not exhibit any of these side effects and hence has weaker toxicity than 4-cholesten-3-one.

INDUSTRIAL APPLICABILITY

The anti-obesity agents of the present invention can inhibit the increase in body weight and the accumulation of body lipids. They are useful due to the little or no side effects and toxicity. Therefore, the anti-obesity agents of the present invention can be used to inhibit the accumulation of body lipids, thereby preventing obesity.

The anti-obesity agents of the present invention can be used to treat obesity, thereby keeping appropriate levels of body weight.

The anti-obesity agents of the present invention can be used to prevent and/or treat various diseases associated with obesity, such as diabetes, hypertension, arteriosclerosis, hyperlipemia, cardiac diseases, nephropathy, gout, fatty liver, gallstone, sleep apnea, osteoarthritis, emmeniopathy, sterility, mammary carcinoma, uterus carcinoma, cancer of rectum, prostatic cancer and the like.

The anti-obesity agents of the present invention can also be used to prevent and/or treat mental disorders associated with obesity, such as bulimia, cibophobia and the like.

The anti-obesity agents of the present invention can also be used to prevent and/or treat obesity and disorders associated with obesity in pet animals such as dogs, cats and the like.

The anti-obesity agents of the present invention can even be used to inhibit the excess accumulation of body lipids in domestic animals and cultured fish, thereby improving the quality of their flesh.

We claim:

1. A food composition comprising an anti-obesity agent selected from the group consisting of 5-cholesten-3-one, 5β-cholestan-3-one, cholesta-4,6-dien-3-one, 6β-bromo-4-cholesten-3-one, 6-hydroxy-4-cholensten-3-one and 4-cholestene-3,6-dione.

2. The food composition of claim 1, wherein the 3-ketosteroid compound is 5-cholesten-3-one.

3. The food composition of claim 1, wherein the 3-ketosteroid compound is 5β-cholestan-3-one.

4. The food composition of claim 1, wherein the 3-ketosteroid compound is cholesta-4,6-dien-3-one.

5. The food composition of claim 1, wherein the 3-ketosteroid compound is 6,β-bromo-4-cholesten-3-one.

6. The food composition of claim 1, wherein the 3-ketosteroid compound is 6-hydroxy-4-cholesten-3-one.

7. The food composition of claim 1, wherein the 3-ketosteroid compound is 4-cholestene-3,6-dione.

* * * * *